United States Patent
Lin et al.

(10) Patent No.: US 9,056,916 B2
(45) Date of Patent: Jun. 16, 2015

(54) METHOD AND ASSAY KIT FOR DETECTION OF TOXICITY INDUCED BY PYRROLIZIDINE ALKALOIDS

(75) Inventors: Ge Lin, Hong Kong (CN); Jiang Zheng, Seattle, WA (US); Na Li, Hong Kong (CN)

(73) Assignee: THE CHINESE UNIVERSITY OF HONG KONG, Hong Kong (CN)

( * ) Notice: Subject to any disclaimer, the term of this patent is extended or adjusted under 35 U.S.C. 154(b) by 288 days.

(21) Appl. No.: 13/354,341

(22) Filed: Jan. 20, 2012

(65) Prior Publication Data

US 2013/0189710 A1    Jul. 25, 2013

(51) Int. Cl.

| C07K 16/00 | (2006.01) |
|---|---|
| C07K 1/04 | (2006.01) |
| C07K 16/44 | (2006.01) |
| G01N 33/53 | (2006.01) |
| G01N 33/567 | (2006.01) |

(52) U.S. Cl.
CPC ............... *C07K 16/44* (2013.01); *G01N 33/53* (2013.01); *G01N 33/567* (2013.01); *G01N 33/5308* (2013.01); *C07K 2317/33* (2013.01)

(58) Field of Classification Search
CPC .................................. C07K 16/44; G01N 33/53
See application file for complete search history.

(56) References Cited

PUBLICATIONS

Roseman et al. Development of a class-specific competitive enzyme-linked immunosorbent assay for the detection of pyrrolizidine alkaloids in vitro. J. Agric. Food CHem. 1992, vol. 40, pp. 1008-1014.*

Roseman et al. Enzyme-linked immunosorbent assay detection of pyrrolilizidine alkaloids: immunogens based on quaternary ppyrrolizidinium salts. Bioconjugate Chem. 1996, vol. 7, pp. 187-195.*

Bober et al. A pyrrolizidine alkaloid enzyme-linked immunosorbent assay detection strategy. ACS Symposium Series; American Chemical Society 1990; pp. 176-183.*

Zundorf et al. Generation and characterization of monoclonal antibodies against the pyrrolizidine alkaloid retrorsine. Planta Medica 1998, vol. 64, pp. 259-263.*

Lin et al., "Hepatic sinusoidal obstruction syndrome associated with consumption of Gynura segeturn," Journal of Hepatology, vol. 54, p. 666-673 (2011).

Fu et al., "Pyrrolizidine Alkaloids—Genotoxicity, Metabolism Enzymes, Metabolic Activation, and Mechanisms," Drug Metabolism Reviews, vol. 36, No. 1, p. 1-55 (2004).

Lin et al., "Characterization of Rat Liver Miorosornal Metabolites of Clivorine, an Hepatotoxic Otoneoine-Type Pyrrolizidine Aikaioid," Drug Metabolism and Disposition, vol. 28, No. 12, p. 1475-1483 (2000).

* cited by examiner

*Primary Examiner* — Shafiqul Haq
(74) *Attorney, Agent, or Firm* — Duane Morris LLP

(57) ABSTRACT

An antibody, which specifically recognizes adducts between pyrrole and cellular macromolecules. Such adducts are likely to occur in mammals suffering an incident of pyrrolizidine alkaloid poisoning. The antibody can be produced using a synthetic immunogen conjugated with a pyrrole as a hapten and it can be used, for example in an assay kit and/or by itself, as a novel means for detecting or diagnosing pyrrolizidine alkaloid poisoning both clinics and research laboratories.

13 Claims, 20 Drawing Sheets

Protein + DHM

X = N or S
R = OH or alkyl group;
Protein = keyhole limpet hemocyanin (KLH), bovine serum albumin (BSA), ovalbumin, fetuin, etc., or their modified protein derivatives Retronecine  Otonecine  Platynecine (A)

(B)

(C)

(D) Antisera of rabbit I
- 16 weeks, $EC_{50}$=31321
- 14 weeks, $EC_{50}$=19245
- 12 weeks, $EC_{50}$=6034
- 10 weeks, $EC_{50}$=4910
- 8 weeks, $EC_{50}$=1498
- 6 weeks (E) Antisera of rabbit II
- 12 weeks, $EC_{50}$=64786
- 10 weeks, $EC_{50}$=31444
- 8 weeks, $EC_{50}$=16223
- 6 weeks, $EC_{50}$=6312
- 4 weeks, $EC_{50}$=947

(F) Antisera of Rabbit III
- 12 weeks, $EC_{50}$=9988
- 10 weeks, $EC_{50}$=5485
- 8 weeks, $EC_{50}$=2884
- 6 weeks (A)

(B)

(A)

(B)

(A)

(B)

(A)

(B)

(A)

(B)

(C)

(A)

(B)

(A)

(B)

(C)

Lane 1: Marker; Lane 2 and 3: control; Lane 4 and 5: treated with retrorsine

Monocrotaline → Dehydromonocrotaline

Protein + DHM

X = N or S
R = OH or alkyl group;
Protein = keyhole limpet hemocyanin (KLH), bovine serum albumin (BSA), ovalbumin, fetuin, etc., or their modified protein derivatives

Lysine-pyrrole

Pyrrole-(NHMe)₂

Chemical Formula: $C_{10}H_{17}N_3$
Molecular Weight: 179.26

Pyrrole-(SMe)₂

Chemical Formula: $C_{10}H_{15}NS_2$
Molecular Weight: 213.36

US 9,056,916 B2

METHOD AND ASSAY KIT FOR DETECTION OF TOXICITY INDUCED BY PYRROLIZIDINE ALKALOIDS

FIELD OF THE INVENTION

The present invention relates to a method for detecting occurrence of toxicity induced by pyrrolizidine alkaloids in mammals. Particularly, it relates to a method and assay apparatus for measuring a toxicity-related intervention between metabolites of pyrrolizidine alkaloids and cellular macromolecules, such as proteins and DNAs, using antibodies specific to the adducts.

BACKGROUND OF THE INVENTION

Pyrrolizidine alkaloids are widely distributed in the nature, existing in about 3% of flowering plants. More than 660 pyrrolizidine alkaloids have been identified from over 6000 plants in three families, Boraginaceae, Compositae, and Legumionsae. Most of the naturally occurring pyrrolizidine alkaloids are known to be hepatotoxic and tumorigenic in animals and humans. Pyrrolizidine alkaloids are generally divided into three types based on the necine bases: retronecine (including its 7-α enantiomer), otonecine, and platynecine, as shown in FIG. 1. The former two types contain unsaturated necine bases and are highly hepatotoxic and genotoxic, while the last type with a saturated necine base are generally thought to be less or non-toxic.

The pyrrolizidine alkaloid-containing plant is likely to be the most common poisonous plants that affect livestock, wildlife, and humans, among which horses, cattle, sheep, goats, swine, chickens, quails, and doves are most susceptible animal species. Acute poisoning causes massive hepatotoxicity with hemorrhagic necrosis. Chronic poisoning takes place mainly in liver, lungs, and blood vessels, and in some instances kidneys, pancreas, gastrointestinal tract, bone marrow, and brain. Prolonged exposures may cause cell enlargement (megalocytosis), veno-occlusion in liver and lungs, fatty degeneration, nuclei enlargement with increasing nuclear chromatin, loss of metabolic function, inhibition of mitosis, proliferation of biliary tract epithelium, liver cirrhosis, nodular hyperplasia, and adenomas or carcinomas.

The earliest case of pyrrolizidine alkaloids-induced intoxication in human was reported in 1920 and associated with the ingestion of pyrrolizidine alkaloid-containing herbal tea. Since then, more than 8000 pyrrolizidine alkaloid-poisoning cases have been documented in many countries, including Afghanistan, Britain, China, Germany, Hong Kong, India, Jamaica, South Africa, Switzerland, and the United States. The most serious known disaster of human pyrrolizidine alkaloid poisoning occurred in 1975 in Northwest Afghanistan, and was associated with the consumption of bread made from wheat flour contaminated with pyrrolizidine alkaloids. Examination of 7200 inhabitants from the affected villages showed evidence of liver disease in 22.6% of those examined. Consumption of pyrrolizidine alkaloid-containing herbs, which may be misused as medicines, or pyrrolizidine alkaloid-contaminated food stuffs, are among the common causes for pyrrolizidine alkaloid-induced intoxication.

Ingestion of pyrrolizidine alkaloids may lead to hepatic sinusoidal obstruction syndrome (HSOS), a clinical syndrome characterized by hepatomegaly, ascites and hyperbilirubinaemia due to sinusoidal congestion caused by pyrrolizidine alkaloids ingestion, haematopoietic stem cell transplantation or solid organ transplantation. The clinical diagnosis of HSOS is largely based on the classical triad of weight gain, painful hepatomegaly and jaundice, however, none of them is specific. The diagnosis of HSOS induced by pyrrolizidine alkaloid-containing herbs was all based on clinical symptoms and on the history of drug/herb exposure reviewed retrospectively. Therefore, a causative diagnosis of HSOS cannot be established because the detailed information on the intake of herbs is unavailable in most of the cases where multi-herb preparations were used. It is known in the art that pyrrolizidine alkaloids themselves are non-toxic, and exert their toxicity by metabolic activation to form the electrophile "pyrrolic" metabolites, which could rapidly react with cellular macromolecules such as protein and DNA (see FIG. 2). The intervention between "pyrrolic" metabolites and macromolecules can be via linkage of either —N— or —S— in different amino acids to form pyrrole-protein and pyrrole-DNA adducts. However, there is no known method for the clinical diagnosis or laboratory determination of pyrrolizidine alkaloid-induced intoxication.

SUMMARY OF THE INVENTION

Accordingly, one object of the present invention is to provide a method for detecting the causative biomarker for confirmative clinical diagnosis or laboratory detection of the intoxication induced by pyrrolizidine alkaloids. Another object of the present invention is to provide an antibody for specifically recognizing tissue-bound pyrroles, or adducts between pyrrole and cellular macromolecules, which may be included in an assay kit for detecting pyrrolizidine alkaloid poisoning.

According to one aspect of the invention, there is provided a method that can be used for detecting or diagnosing pyrrolizidine alkaloid poisoning in a mammal, comprising steps of (a) taking a biological specimen from said mammal and (b) conducting an immunoassay with said specimen using an antibody having antigen binding site recognizing a pyrrole moiety conjugated on a cellular macromolecule. Preferably, the cellular macromolecule is a protein, DNA or RNA. The immune assay preferably is an enzyme-linked immunoabsorbent assay (ELISA), Western blot, or an immunohistochemical method.

According to another aspect of the present invention, there is provided an antibody, which comprises a binding site specific to a pyrrole moiety in adducts between metabolites of pyrrolizidine alkaloids and cellular macromolecules, such as proteins or DNAs. The antibody may be raised in a mammal administered with a synthetic immunogen comprising a pyrrole moiety as hapten and a carrier protein.

As it would be understandable to a person of ordinary skill, other method may be used to produce antibody against the pyrrole moiety carrying immunogen. For the carrier proteins, a preferred one is keyhole limpet hemocyanin (KLH), although other carriers may also provide satisfactory results as long as it has a sufficiently large size and enough lysine or cysteine or other amino acid residuals to conjugate the hapten as well as other considerations readily come to the mind of a person of ordinary skill. The hapten can be any species as long as it have the following moiety:

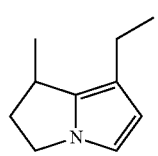

Accordingly a further aspect of the present invention, there is provided an assay kit, which comprises antibody that has a binding site specific to a pyrrole moiety in adducts between metabolites of pyrrolizidine alkaloids and cellular macromolecules, such as proteins or DNAs. The assay kit, based on an antibody-antigen reaction, are capable of providing a quick and convenient detection for pyrrolizidine alkaloids-induced intoxication, both for clinical or laboratory uses.

For the purpose of the present invention, the term "antibody" refers to the polycolonal antibody or the monoclonal antibody and the term "pyrrole moiety" means a chemical structure defined by the following formula (as part of the molecules shown in FIG. 2):

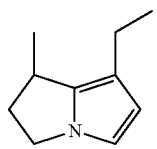

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DISCRETION OF THE INVENTION

General Considerations

Figure 1:
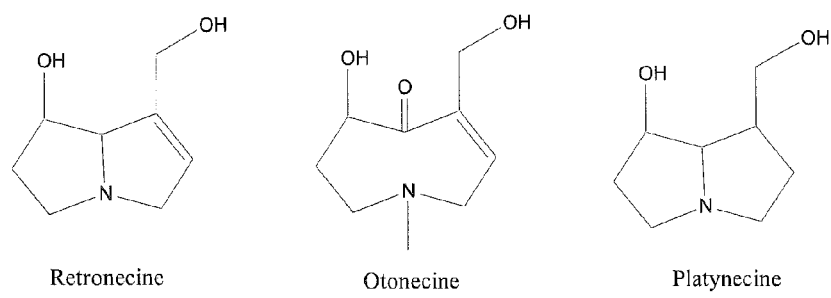
FIG. 1 shows the common necine bases of pyrrolizidine alkaloids.
Figure 2:
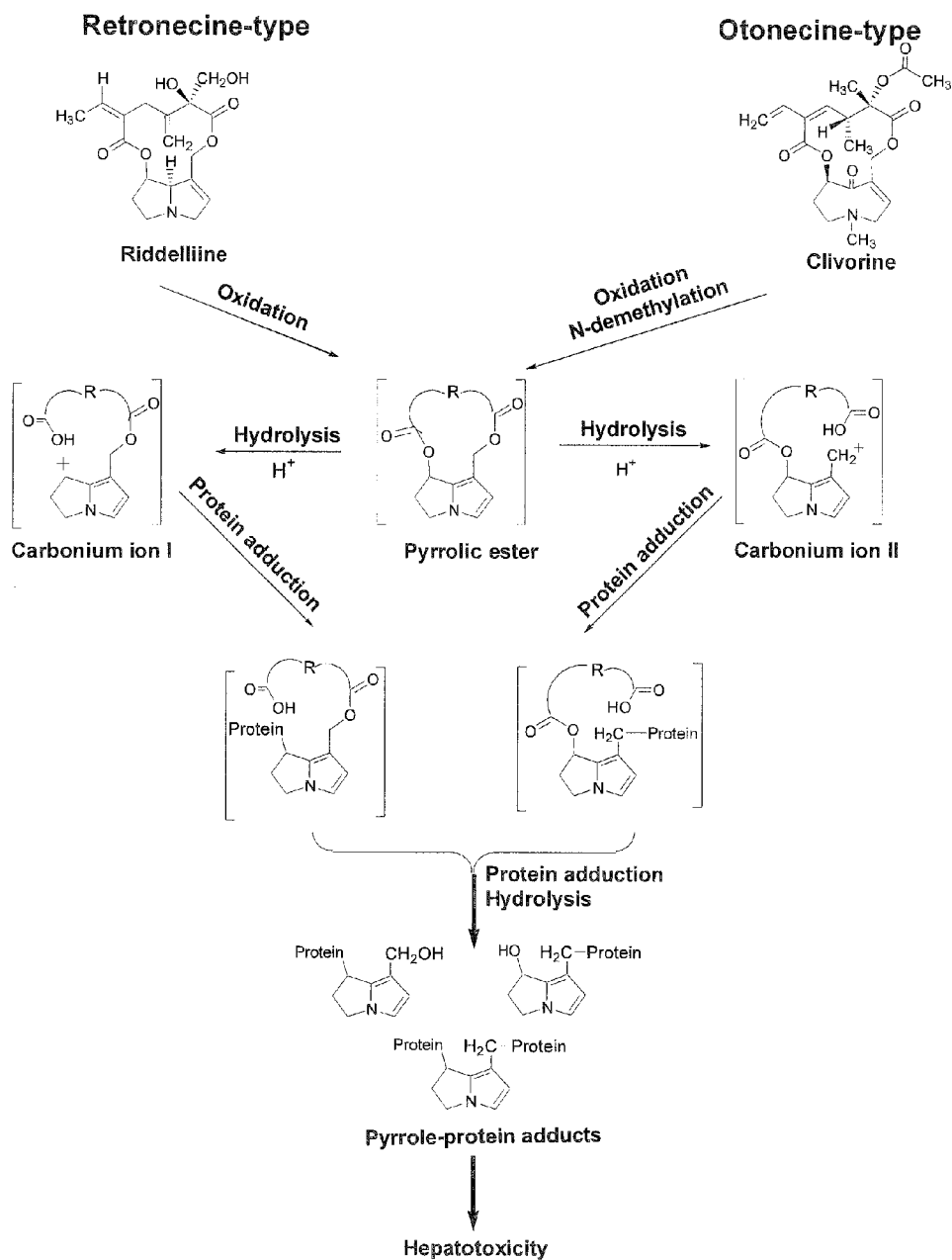
FIG. 2 shows the process of the metabolic activation of retronecine- and otonecine-type pyrrolizidine alkaloids leading to hepatotoxicity.

The method is based on hypothesis that the formation of tissue-bound pyrroles can be developed as a biomarker for a rapid assessment of pyrrolizidine alkaloid-induced hepatotoxicity. The basis of the hypothesis is inventors' preliminary data that have demonstrated that (1) the degree of hepatotoxicity varies after exposure to various pyrrolizidine alkaloids; (2) a portion of pyrrolic metabolites of different pyrrolizidine alkaloids formed in the liver can migrate to the blood circulation and covalently bind to blood protein forming pyrrole-protein adducts; (3) pyrrole-derived protein adducts are released to the circulation due to hepatocyte injury; and (4) pyrrolizidine alkaloid-induced toxicity associates with tissue-bound pyrroles in the liver and pyrrole-derived protein adducts in the blood. Therefore, a method capable of detecting the level of pyrrole-derived protein adducts or pyrrole-derived DNA adducts would for the first time provide a means for quick, convenient clinical diagnosis or laboratory determination of pyrrolizidine alkaloid-induced intoxication.

In present invention, an immunoassay technique, which uses antibody and antigen complexes as a means of generating a measurable result, was chosen as the means for detecting the pyrrole-derived adducts. In order to decrease the non-specific response, the antibody raised with a particularly designed immunogen of the present invention was purified by affinity columns. Furthermore, two purified antibodies, referred to as N-antibody and S-antibody, were also obtained to more specifically determine the pyrrole adducts via N- and S-linkage, respectively.

The raised antibody and two purified antibodies are applied for the detection of pyrrole-derived protein adducts in the experimental animals. Male SD rats or mice are administrated with pyrrolizidine alkaloids, senecionine and seneciphylline-containing *Gynura segetum* or pyrrolizidine alkaloid-free *Sedum aizoon*. After 24 hours of administration, the liver and blood samples are collected. The hepatotoxicity is assessed by the elevation of serum ALT levels and liver histomorphological changes. The results of competitive ELISA, Western blot and competitive Western blot show that the antibodies produced according the present invention can be suitable to be used as a tool to determine the protein adduction induced by pyrrolizidine alkaloids.

The antibody is purified with two affinity columns, one is CarboxyLink-pyrrole column and another is ThioLink-pyrrole column. The core moiety is the pyrrole moiety, and thus the material used for the separation is not limited to Carboxy-Link and ThioLink resins.

Design of Immunogen

In a particular embodiment of this invention, the antibody was raised by immunizing the female New Zealand rabbits with the synthetic immunogen, which is a KLH-pyrrole adduct. While keyhole limpet hemocyanin (KLH) was used in the embodiment as the carrier protein, as it would be readily understandable to a person of ordinary skill in the art, other carrier proteins may also produce satisfactory results in practicing the present invention. In general, any the carrier proteins that have a sufficiently large size and a large number of lysine or cysteine or other amino acid residuals for conjugation with the hapten, which in this case is the pyrrole moiety (2,3-dihydro-1H-pyrrolizine).

Preparation of Immunogen and Coating Antigen

Figure 21:
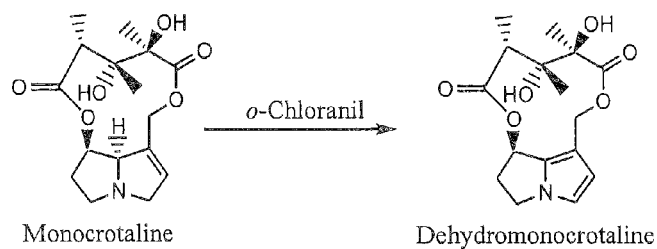
FIG. 21 shows the chemical scheme of making dehydromonocrotaline (DHM).

To monocrotaline (20 mg) dissolved in chloroform (5 mL) was added a solution of o-chloranil (25 mg) in chloroform (5 mL). After 5 min, TLC (Thin layer Chromatography) showed that most of starting material was consumed and the mixture was shaken vigorously with a cooled (0-5° C.) solution, which contained 700 mg KOH and 20 mg $NaBH_4$ in 1 mL water for 10-15 sec. The organic phase was separated, immediately dried with anhydrous $Na_2SO_4$ and concentrated under reduced pressure to give dehydromonocrotaline (DHM). The chemical reaction was depicted in FIG. 21.

Figure 22:
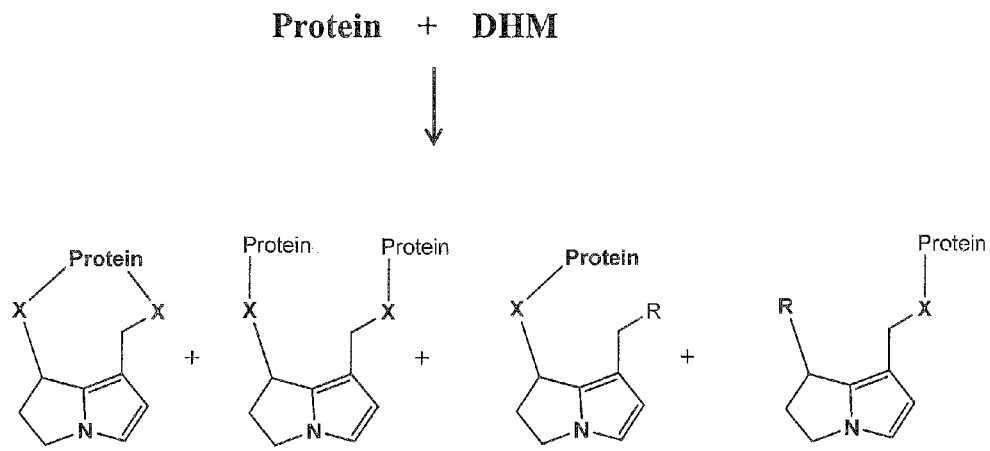
FIG. 22 shows the process of preparing immunogens and coating antigens.

A solution (2 mL) containing KLH (10 mg/mL) in phosphate buffer (PBS, pH 7.4) was mixed with 20 mg of DHM in 125 μL of DMSO. The pH of the reaction mixture was adjusted to 9-10 with 0.1 N NaOH, and the reaction was performed overnight under nitrogen while stirring. The next day, the reaction mixture was dialyzed three times against 1 L of deionized water and dried by lyophilization. The coating antigen, bovine albumin-pyrrole adducts (BSA-pyrrole adducts), was synthesized using the same method as detailed above except that BSA was used instead of KLH. The underlying reactions of conjugation are shown in FIG. 22.

Preparation of Competitors

Figure 23:
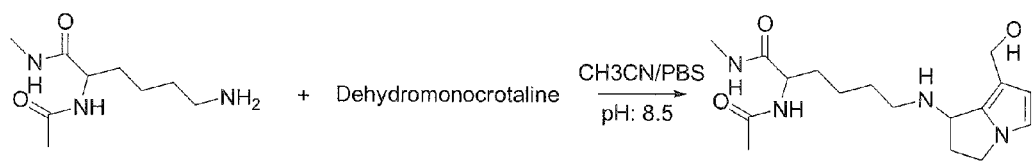
FIG. 23 shows the process of making competitors.
Figure 23:
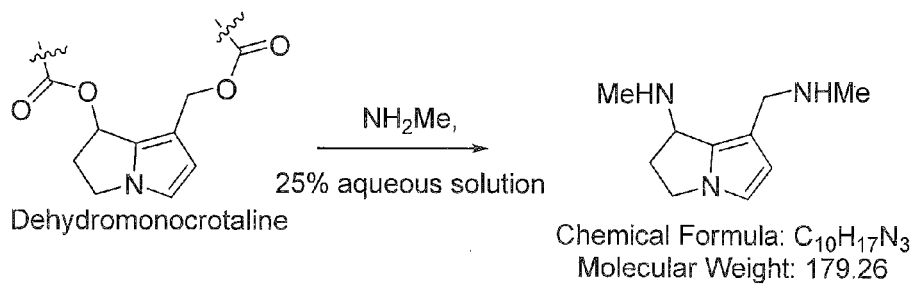
Figure 23:
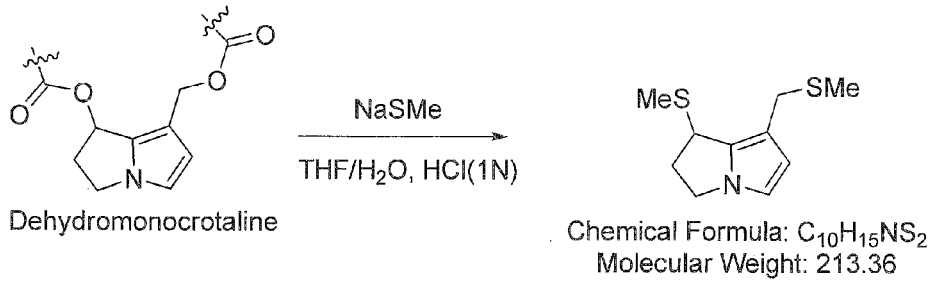

N-Acetyl-L-lysine-pyrrole was prepared as shown in FIG. 23. Specifically, the process is as follows. DHM (9.7 mg, 0.03 mmol) was dissolved in DMSO (100 μL). To the solution was added N-acetyl-L-lysine (56 mg, 0.3 mmol) in 1 mL water. The reaction mixture was stirred at room temperature for 3-5 h, and neutralized with 0.05 N NaOH. The organic solvent was removed under reduced pressure, and the residue was directly subjected to HPLC for further purification.

To produce pyrrole-$(SMe)_2$, DHM was dissolved in THF, to which NaSMe in 1 N HCl solution was then added. The reaction mixture was stirred at room temperature to produce the sulfur analyte, pyrrole-$(SMe)_2$.

The nitrogen analyte, pyrrole-$(NHMe)_2$, was prepared by mixing DHM with $NH_2Me$ in 25% aqueous solution.

The processes of preparing these competitors are shown in FIG. 23.

Preparation of Antibody

Three female New Zealand rabbits weighing 2.5-3.0 kg were immunized with the immunogen prepared above. The immunogen (100 mg) was dissolved in 0.5 mL of distilled water and emulsified with 0.5 mL of Freund's complete adjuvant. The rabbits were injected subcutaneously with the emulsion of immunogen (1 mL/rabbit) at multiple sites in the back. After 2 weeks, the animals were boosted several times with a two-week interval by the same procedure, except that Freund's incomplete adjuvant was used instead of Freund's complete adjuvant. The rabbits were boosted until no further increase in antibody titer was observed.

Titration of Antibody

The titer of the serum obtained from the rabbits immunized by the immunogen was determined by measuring the binding of serial dilutions (1/100 to 1/204,800) to microtiter plates coated with BSA-pyrrole adducts. Coating antigen solution (100 μL) in PBS buffer (200 mM, pH 7.4) containing BSA-pyrrole adducts (20 mg/mL) was added to each well of a 96-well microtiter plate. Plates were incubated at 4° C. overnight or room temperature for 2 h. Then, the plates were washed three times by a PBST buffer (200 mM PBS containing 0.05% Tween-20 at pH 7.4). After washing, 150 μL of 5% nonfat milk in PBS buffer was added to each well and incubated at room temperature for 1.5 h, followed by the washing three times with PBST buffer. Then, the antiserum in PBST buffer at various dilutions was added (100 mL per well) to the plates and incubated at room temperature for 2 h. After washing in the same manner, 100 mL of anti-rabbit IgG-horseradish peroxidase solution in PBST buffer (1/10,000) was added to each well, and incubated for 1 h at room temperature. The plates were washed again as described previously. To each well, 100 μL of freshly prepared substrate solution containing 0.3 mM tetramethylbenzidine (TMB) and 0.1 mM $H_2O_2$ in 0.1 M sodium acetate buffer (pH 5.5) was added and incubated for about 5-30 min at room temperature. The colorimetric development was quenched by adding 50 μL of a 4 N sulfuric acid solution to each well. The absorbance at dual wavelengths (450-650 nm) was read. Higher absorbance value corresponds to stronger immune response between the coating antigen and the rabbit serum, i.e. higher content of antibody produced in rabbit blood. Similar procedure was also applied to determine the reaction between antiserum with native BSA and between rabbit blank serum with the coating antigen.

Figure 3:
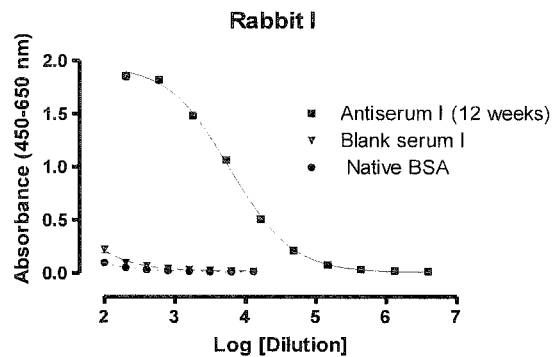
FIG. 3 shows titration tests of antisera I, II and III prepared from three rabbits, respectively.
Figure 3:
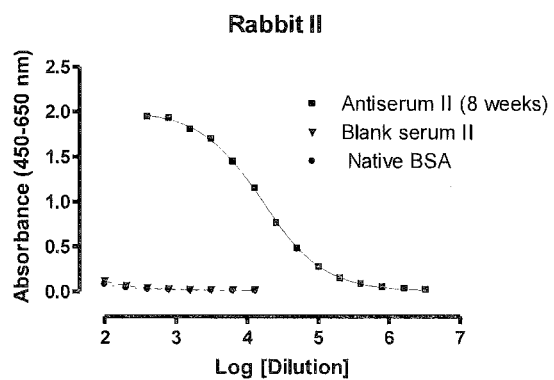
Figure 3:
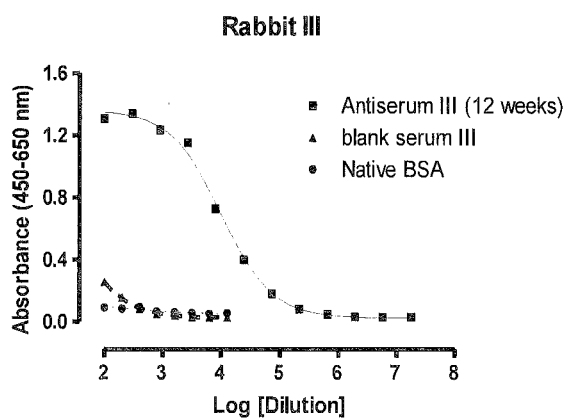
Figure 3:
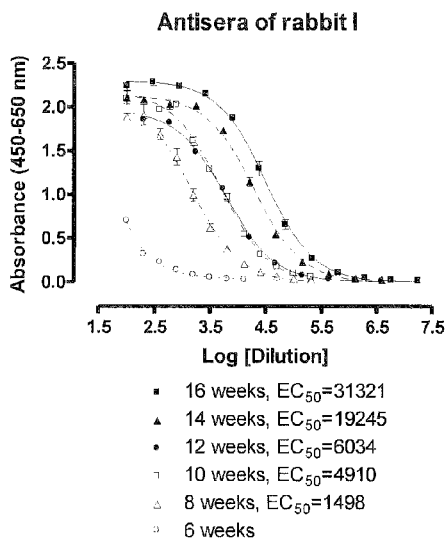
Figure 3:
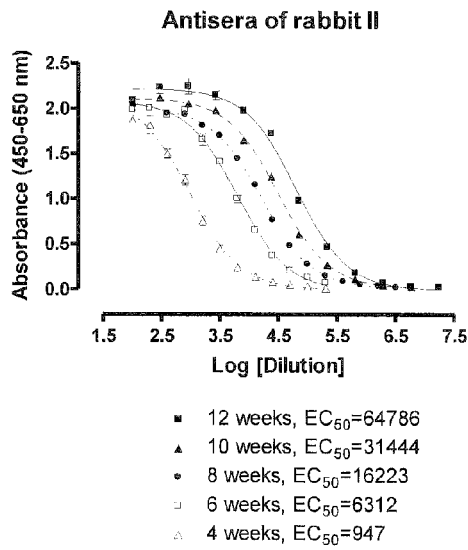
Figure 3:
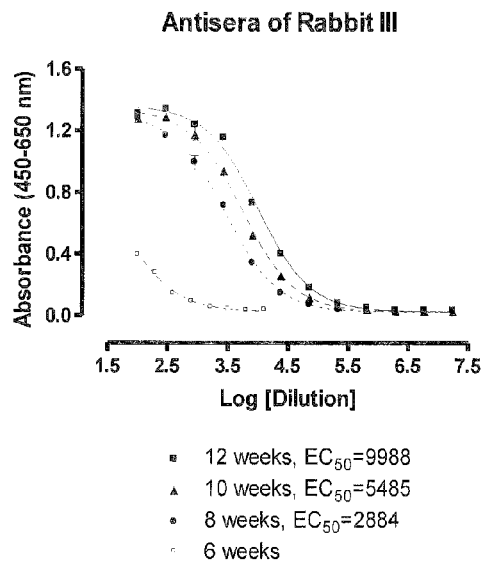

As shown in FIG. 3, significant immune responses were observed in all three rabbits starting from 2, 4, and 8 weeks of immunization in rabbits I, II, and III, respectively, and the immune response increased with the immunization time (FIG. 3D-3F). No immune response was observed between the antiserum and native BSA and between blank rabbit serum and the coating antigen (FIG. 3A-3C), indicating that the antibody against the designed hapten was produced by the immunization. Finally the antibody-containing blood samples in rabbits I, II and III were harvested after about 17, 12 and 17 weeks of immunization when the antibody production reached a plateau in individual rabbits.

Specificity of Antibody

The specificity of antibody was evaluated with competitive ELISA and Western blot assays using antiserum II as a representative.

Figure 4:
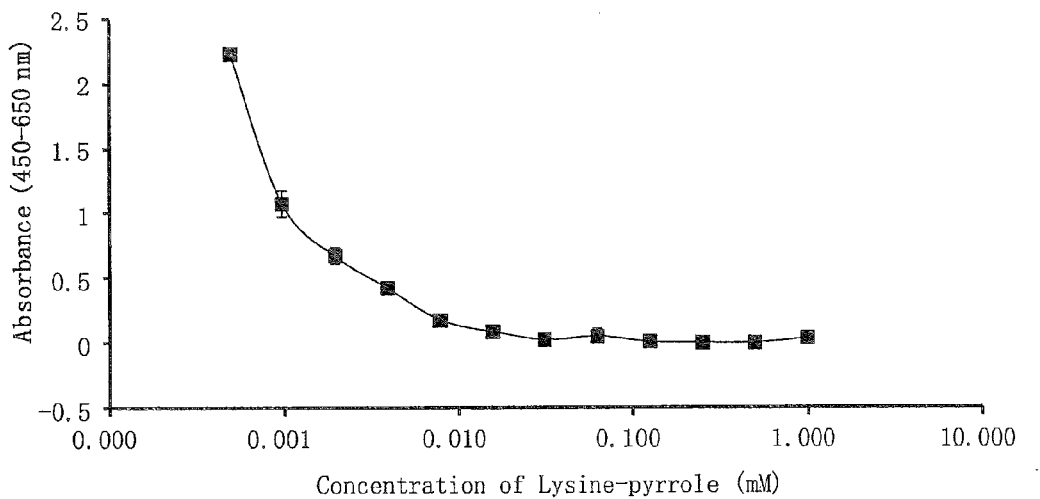
FIG. 4 shows a competitive ELISA assay of antiserum II using N-acetyl-L-lysine-pyrrole as competitor.
Figure 5:
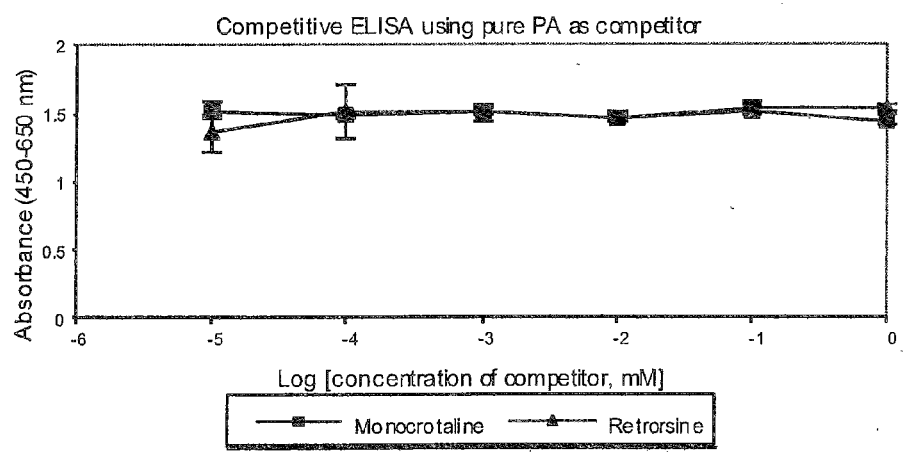
FIG. 5 shows a cross-reactivity test of antiserum II (1:30000) with monocrotaline and retrorsine.

In competitive ELISA assay, one hundred microliters of coating antigen, BSA-pyrrole adducts, in PBS buffer was added to wells of a 96-well microtiter plate. The plates were incubated at 4° C. overnight or room temperature for 2 h. Serial dilutions of the competitor, N-acetyl-L-lysine-pyrrole, were prepared in PBST buffer. The resulting solution was mixed (1:1 v/v) with diluted antiserum in 5% nonfat milk dissolved in PBST buffer. The mixture was incubated at 4° C. overnight. The following day, the same procedure as in the titer analysis was followed. The absorbance at dual wavelength (450-650 nm) was read. The cross activity with pure PAs was also determined using the same procedure, except pure PAs, retrorsine or monocrotaline, instead of N-acetyl-L-lysine-pyrrole. The results showed that the immune response between the coating antigen and antiserum II was completely inhibited by N-acetyl-L-lysine-pyrrole in a concentration-dependent manner (FIG. 4). Moreover, no cross-reactivity was observed for monocrotaline and retrorsine (FIG. 5). These results indicated that antiserum II might contain the antibody specifically recognized the pyrrole moietyin.

Figure 6:
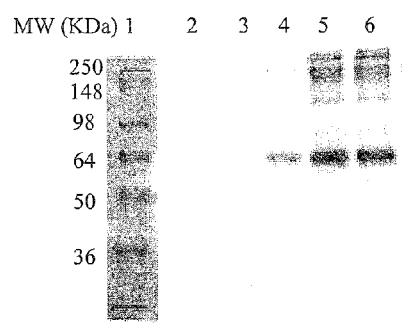
FIG. 6 shows the result of a Western blot assay of antiserum II. Lane 1: marker; Lane 2: native BSA; Lane 3: BSA/BSA-pyrrole 9:1; Lane 4: BSA/BSA-pyrrole 1:1; Lanes 5 and 6: BSA-pyrrole. 2 µg of proteins were loaded.

In Western blot assay, protein bands were resolved by 7.5% SDS-PAGE (polyacrylamide gel electrophoresis) and then transferred to nitrocellulose membranes (Amersham International Plc, England). Four different samples, native BSA, coating antigen, and the mixtures of native BSA and coating antigen at ratios of 9:1 and 1:1, were loaded. Before loading, a protein assay was conducted to ensure that an equal amount of protein was loaded. Blots were then blocked with 5% nonfat milk in PBST buffer for 1 h at room temperature. Blotted membranes were incubated with 1/5000 dilution of antiserum II in PBST buffer with 5% nonfat milk at 4° C. overnight. The following day, after washing three times with PBST buffer, membranes were incubated with anti-rabbit IgG-horseradish peroxidase solution (1/3000 in PBST buffer with 5% nonfat milk) for 1 h at room temperature. After washing, protein bands were detected by chemiluminescence with an ECL detection kit (Cell Signaling Technology, Danvers, Mass.). As shown in FIG. 6, a chemiluminescent band at about 64 KDa was observed in the lanes loaded with BSA-pyrrole adducts. In addition, the BSA-pyrrole adducts without native BSA dilution produced the highest chemiluminescence, followed by those protein adducts diluted with 2- and 10-fold native BSA, while no chemiluminescent band was observed in the lane loaded with the same amount of native BSA. This further indicated that the antibody are able to detect protein adducts derived from pyrrole in a concentration-dependent manner and show no cross-reaction toward the native protein.

Purification of Antibody to Produce N-Antibody

Figure 7:
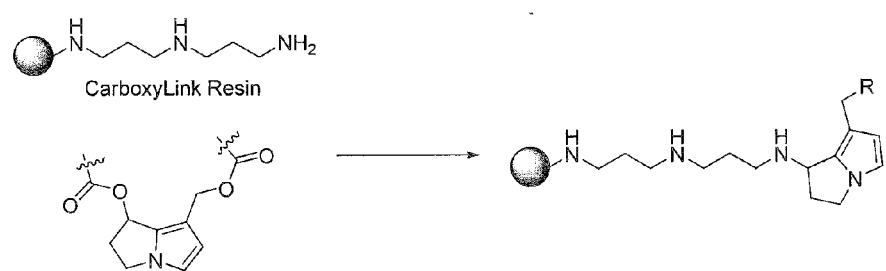
FIG. 7 shows the step of preparing CarboxyLink-pyrrole affinity column.
Figure 8:
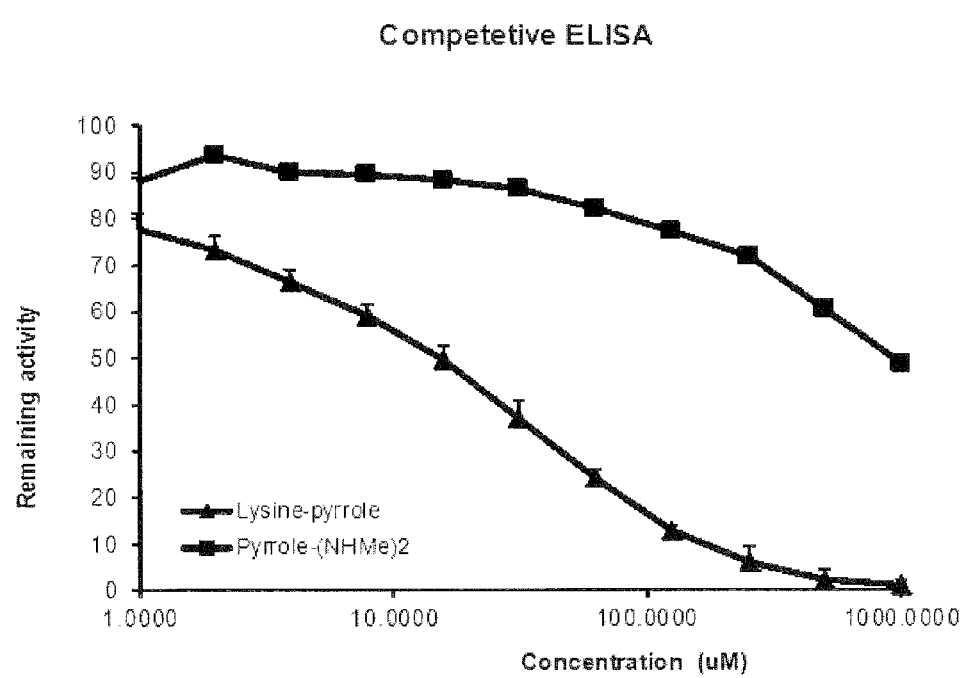
FIG. 8 is a competitive ELISA of purified N-antibody using lysine-pyrrole and pyrrole-(NHMe)$_2$ as competitors.

N-antibody was purified by CarboxyLink-pyrrole affinity column, which was prepared as follows (See FIG. 7). Four milliliters of CarboxyLink™ coupling gel slurry (Pierce Biotechnology, Rockford, Ill.) was washed with 5 mL of PBS twice and then transferred into the reaction flask. DHM (10 mg) dissolved in 400 μL of DMSO was added into the reaction flask and the reaction was performed at room temperature overnight. Then, the pyrrole-linked resin slurry was packed into the column and allowed to drain. The column was washed with 5 mL PBS (pH 7.4) twice, and settled for 30 minutes prior to use.

One hundred microliters of antiserum II was diluted with 1 mL PBS (pH 7.4) and applied to the column. After the antiserum solution completely entered the gel bed, additional 0.5 mL PBS was added and allowed to enter the gel bed. Capped the bottom of the column, the antiserum was incubated for 2 h at room temperature while mixed gently end-over-end. After incubation, the column was consecutively washed with 10 mL of PBS (pH 7.4) and 2 M NaCl-containing PBS (pH 7.4). Then, the antibody was flushed out with glycine buffer (100 mM, pH 2.5-3.0) and collected in 1 mL eppendorf tubes. The fractions were neutralized by adding 0.5 mL of 1 M Tris (pH 9.0). The elution was dialyzed against 1 L PBS buffer at 4° C. for three times. Aliquot the purified antibody in 500 μL in small vials and kept at −20° C. for further use. The antibody purified this way is referred to as "N-antibody" and more specifically recognizes the pyrrole moiety with N-linkage in the pyrrole-protein adducts in the present invention.

Specificity of N-antibody

The specificity of N-antibody was evaluated with competitive ELISA, Western blot and competitive Western blot assays.

In competitive ELISA assay, one hundred microliters of coating antigen, BSA-pyrrole adducts, in PBS buffer was added to wells of a 96-well microtiter plate. The plates were incubated at 4° C. overnight or room temperature for 2 h. Serial dilutions of the competitor, N-acetyl-L-lysine-pyrrole, were prepared in PBST buffer. The resulting solution was mixed (1:1 v/v) with diluted antiserum in 5% nonfat milk dissolved in PBST buffer. The mixture was incubated at 4° C. overnight. The following day, the same procedure as in the titer analysis was followed. The absorbance at dual wavelength (450-650 nm) was read. The cross activity with pure PAs was also determined using the same procedure, except pure PAs, retrorsine or monocrotaline, instead of N-acetyl-L-lysine-pyrrole. The results showed that the immune response between the coating antigen and antiserum II was completely inhibited by N-acetyl-L-lysine-pyrrole in a concentration-dependent manner (FIG. 4). Moreover, no cross-reactivity was observed for monocrotaline and retrorsine (FIG. 5). These results indicated that antiserum II might contain the antibody specifically recognized the pyrrole moiety in the pyrrole-protein adducts.

Figure 9:
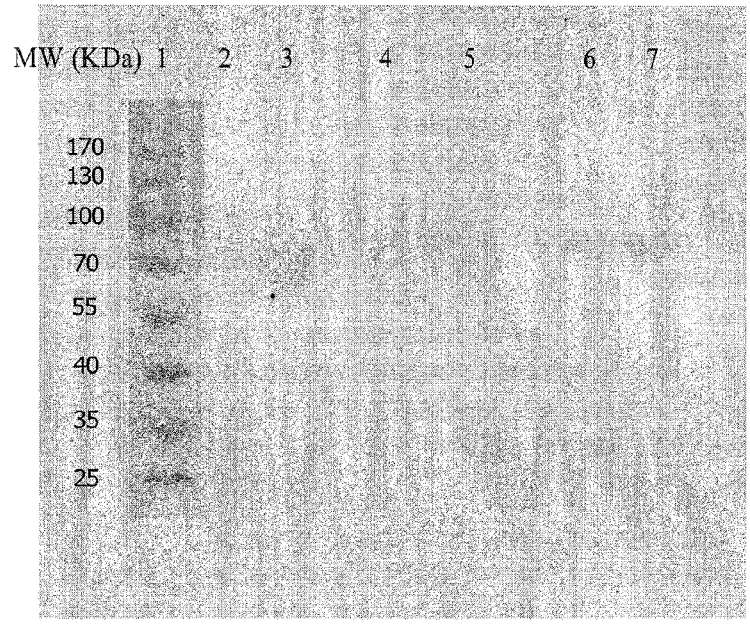
FIG. 9 is a competitive Western Blots of purified N-antibody using pyrrole-(NHMe)$_2$ as competitor. Lane 1: Marker; Lane 2: BSA; Lane 3: BSA-pyrrole; Lane 4 and 5: BSA-pyrrole as loading antigen and 1 mM pyrrole-(NHMe)$_2$ as competitor; Lane 6 and 7: BSA-pyrrole as loading antigen and 0.1 mM pyrrole-(NHMe)$_2$ as competitor.
Figure 9:
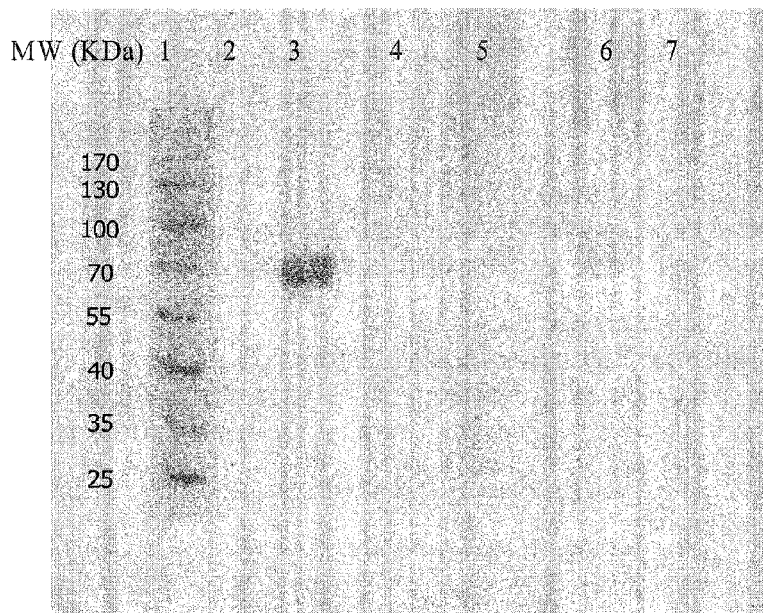

In Western and competitive Western blot assay, coating antigen was loaded and resolved by 7.5% SDS-PAGE and then transferred to nitrocellulose membranes. Blots were then blocked with 5% nonfat milk in PBST buffer for 1 h at room temperature. Blotted membranes were incubated with 1/4000 dilution of purified N-antibody in PBST buffer with 5% nonfat milk in the absence or 0.1 mM or 1 mM of pyrrole-$(NHMe)_2$ at 4° C. overnight. The following day, after washing three times with PBST buffer, membranes were incubated with anti-rabbit IgG-horseradish peroxidase solution (1/5000 in PBST buffer with 5% nonfat milk) for 1 h at room temperature. After washing, protein bands were detected by chemiluminescence with an ECL detection kit. The Western blot results also showed that the purified N-antibody had the immune response with BSA-pyrrole adducts, while no response with native BSA. Moreover, the immune response was inhibited by pyrrole-containing competitor, pyrrole-$(NHMe)_2$, in competitive Western blot assays, and the inhibitory effect was concentration-dependent manner (FIG. 9).

These results indicated that the purified N-antibody specifically recognized the pyrrole moiety, in particular the pyrrole moiety via N-linkage, in the pyrrole-protein adducts.

Purification of Antibody to Produce S-Antibody

Figure 10:
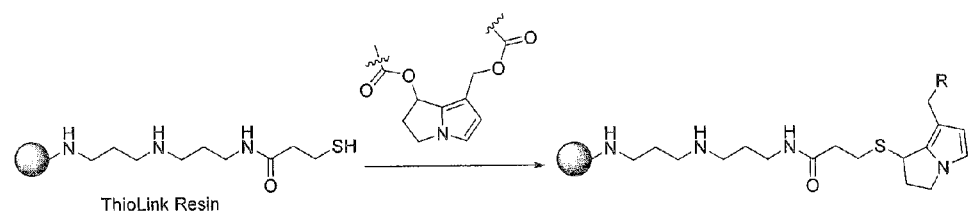
FIG. 10 shows the step of preparing ThioLink-pyrrole affinity column.

S-antibody was purified by ThioLink-pyrrole affinity column, which was prepared as follows (See FIG. 10). Except for using a different affinity column, the procedure was the same for the aforementioned N-antibody purification.

Specificity of S-Antibody

The specificity of S-antibody was evaluated with Western blot and competitive Western blot assays.

Figure 11:
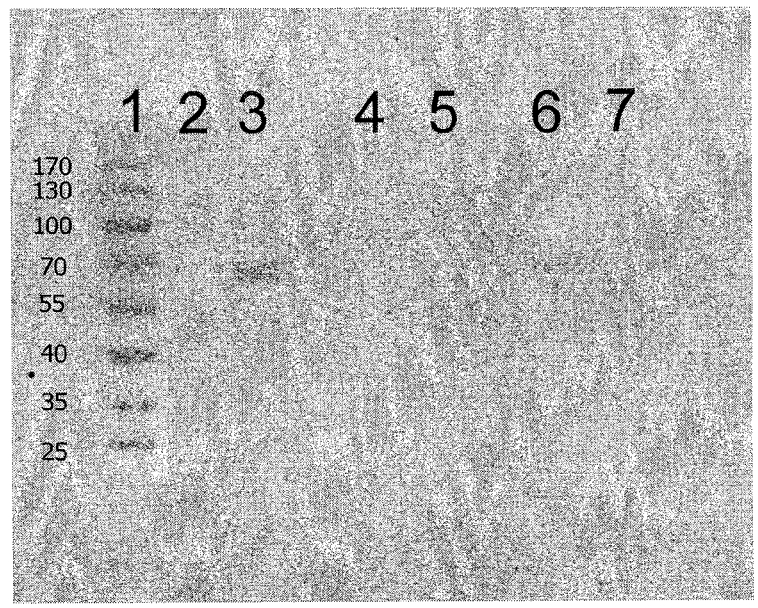
FIG. 11 is a competitive Western Blots of purified S-antibody using pyrrole-(SMe)$_2$ as competitor. Lane 1: Marker; Lane 2: BSA; Lane 3: BSA-pyrrole; Lane 4 and 5: BSA-pyrrole as loading antigen and 1 mM pyrrole-(SMe)$_2$ as competitor; Lane 6 and 7: BSA-pyrrole as loading antigen and 0.1 mM pyrrole-(SMe)$_2$ as competitor.
Figure 11:
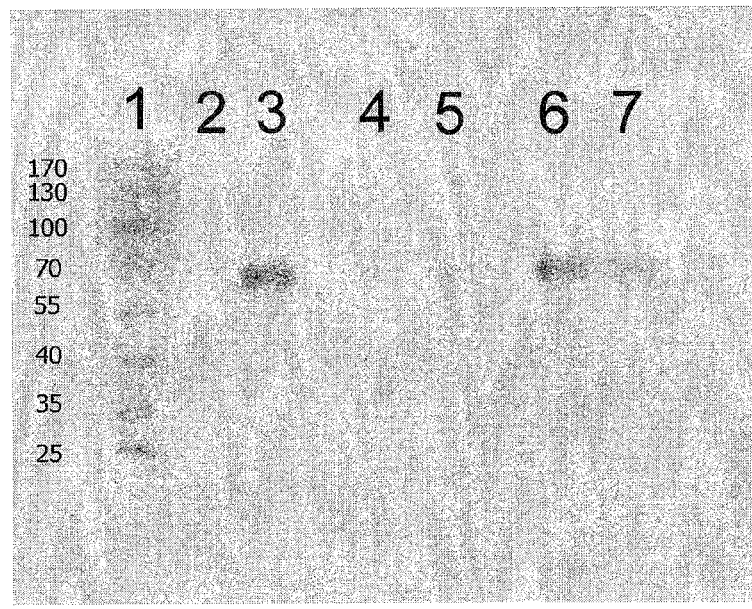

In Western and competitive Western blot assay, coating antigen was loaded and resolved by 7.5% SDS-PAGE and then transferred to nitrocellulose membranes. Blots were then blocked with 5% nonfat milk in PBST buffer for 1 h at room temperature. Blotted membranes were incubated with 1/4000 dilution of purified S-antibody in PBST buffer with 5% nonfat milk in the absence or 0.1 mM or 1 mM of pyrrole-$(SMe)_2$ at 4° C. overnight. The following day, after washing three times with PBST buffer, membranes were incubated with anti-rabbit IgG-horseradish peroxidase solution (1/5000 in PBST buffer with 5% nonfat milk) for 1 h at room temperature. After washing, protein bands were detected by chemiluminescence with an ECL detection kit. The Western blot results also showed that the purified S-antibody had the immune response with BSA-pyrrole adducts, while no response with native BSA. Moreover, the immune response was inhibited by pyrrole-containing competitor, pyrrole-$(SMe)_2$, in competitive Western blot assays, and the inhibitory effect was concentration-dependent manner (See FIG. 11). These results indicate that the purified S-antibody specifically recognized the pyrrole moiety, in particular the pyrrole moiety via S-linkage, in the pyrrole-protein adducts.

Determination of Pyrrole-Derived Protein Adducts in Liver Samples of Rats

Male SD rats (body weight, 190-220 g) were supplied by the Laboratory Animal Services Centre at The Chinese University of Hong Kong. Animals were placed in a controlled environment (50% relative humidity, temperature of 25° C. and dark/light cycles) and allowed access to standard rat chow and water. Herbal extracts were prepared via extracting the powdered herbal samples with distilled water for three times followed by drying the combined water extracts under reduced pressure. The obtained residues were reconstituted into the aqueous sulfuric acid solution and extracted with hexane to remove non-alkaloid components. The aqueous layer was adjusted to pH 9-10 and then extracted with dichloromethane for three times. The combined dichloromethane filtration was evaporated to provide the alkaloid extract. The total content of toxic pyrrolizidine alkaloids in the extracts was quantified by our previously developed HPLC analytical methods. Stock solutions were prepared as follows. Retrorsine, *Gynura segetum* or *Sedum aizoon* alkaloid extract (100 mg) was suspended in 1 mL of distilled water, and the resulting suspension was acidified by adding dilute HCl solution until PAs were dissolved. The resultant solution was neutralized with dilute NaOH solution, followed by addition of water to appropriate concentration. Rats in treatment groups (n=5) were orally treated with a single dose of retrorsine (35, 70, 140, and 280 mg/kg, i.e. 0.1, 0.2, 0.4 and 0.8 mmol/kg) or *G. segetum* alkaloid extract (192 mg/kg, i.e. 0.5 mmol of pyrrolizidine alkaloid/kg) or *S. aizoon* alkaloid extract (192 mg/kg) or cyclophosphomide (56 mg/kg), which was used as a positive control to induce hepatotoxicity. While the ones in control group (n=5) were administered with vehicle (distilled water) correspondingly. At 24 hours after administration, blood samples were collected by cardiac puncture after anesthetizing the rats with diethylether, and liver samples were removed from rats immediately after sacrifice by cervical dislocation. Serum ALT (alanine aminotransferase) activities were measured following the Sigma's protocol. Liver histomorphology was assessed by standard hematoxylin-eosin (H&E) staining procedures.

Figure 12:
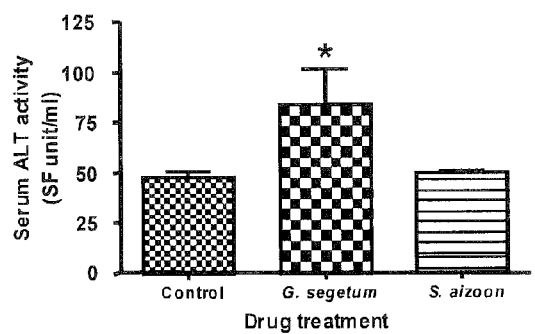
FIG. 12 shows the effects of alkaloid extracts of *Gynura segetum* and *Sedum aizoon* with a single oral treatment on serum ALT level (A) and liver histomorphological changes (B) in rats. *$p<0.05$ compared with control and *S. aizoon* treated groups (One-way ANOVA for comparison among three groups). SF unit: Sigma-Frankel unit. CV: central vein; Bar=200 µm. Mild hemorrhage in the centrilobular region of the *G. segetum* treated rat indicated by arrows.
Figure 12:
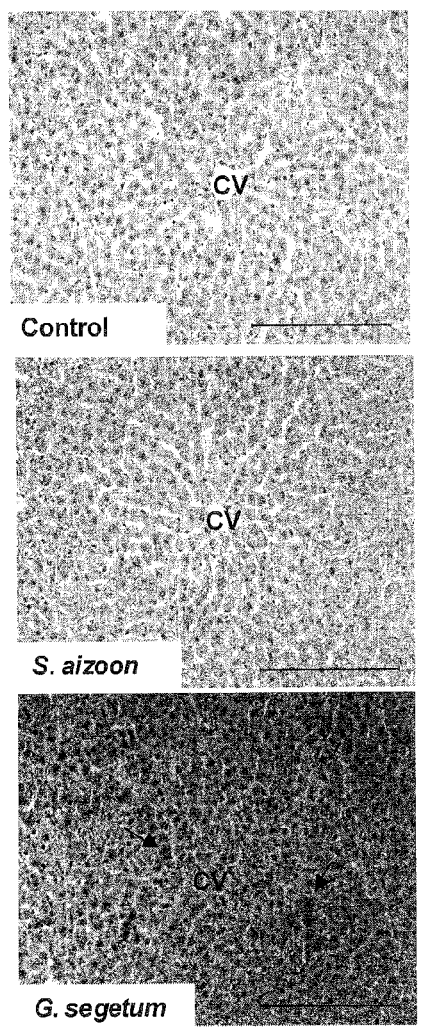

The liver samples were homogenized in lysis buffer or normal saline, while blood (plasma or serum) samples were directly subjected to the analysis. Significant increase of serum ALT level was observed in the treated rats and H&E staining exhibited the hemorrhage in the centrilobular region of liver, as shown in FIG. 12, demonstrating that the hepatotoxicity had been induced by pyrrolizidine alkaloids.

The pyrrole-bound protein adducts in the liver samples of rats treated with pyrrolizidine alkaloids were detected by Western blot and competitive ELISA assays.

Figure 13:
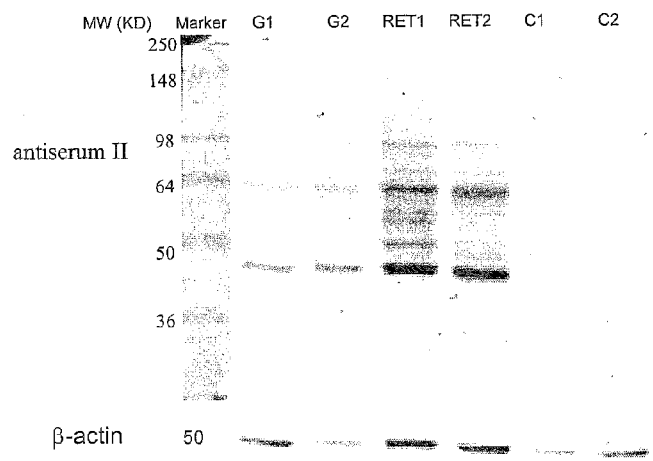
FIG. 13 is a Western blot assay of rat liver samples detected by antiserum II. (A) G1 and G2: livers of 2 rats treated with *G. segetum* alkaloid extract (192 mg/kg); RET1 and RET2: livers of 2 rats treated with retrorsine (280 mg/kg); C1 and C2: livers of 2 control rats; (B) R0.1, 0.2, 0.4, and 0.8=livers of rats treated with retrorsine at different dosages (35, 70, 140, and 280 mg/kg); C1 and C2: livers of 2 control rats.
Figure 13:
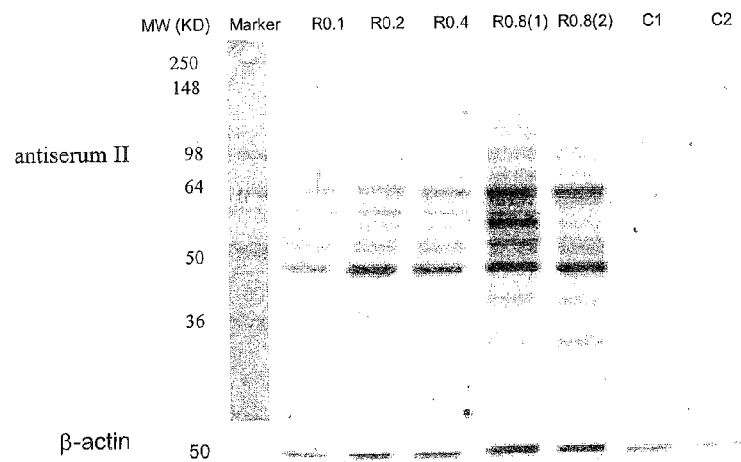

In Western blot assay, rat liver lysates were loaded and resolved by 7.5% SDS-PAGE and then transferred to nitrocellulose membranes. Before loading, a protein assay was conducted to ensure that an equal amount of protein was loaded. The blots were blocked with 5% nonfat milk in PBST buffer for 1 h at room temperature. Blotted membranes were incubated with 1/5000 dilution of antiserum II in PBST buffer with 5% nonfat milk at 4° C. overnight. The following day, after washing three times with PBST buffer, membranes were incubated with anti-rabbit IgG-horseradish peroxidase solution (1/3000 in PBST buffer with 5% nonfat milk) for 1 h at room temperature. After washing, protein bands were detected by chemiluminescence with an ECL detection kit. β-Actin served as internal standard. Briefly, when the detection of pyrrole-protein adducts completed, the same membrane was incubated with stripping buffer at 50° C. for 30 min to remove the antibody against pyrrole-protein adducts. Then β-actin was similarly detected using anti-β-actin monoclonal antibody (1/3000 dilution) and anti-rabbit IgG-horseradish peroxidase (1/2000 dilution) as primary and secondary antibodies, respectively. The pyrrole-protein adducts were determined by the antiserum II. Several bands, which were not found in control rats, were detected from the liver samples of rats treated with retrorsine and *G. segetum* (FIG. 13A), especially the two bands at about 45 and 98 KD. And some of them seemed to be dose-related, e.g. two bands label with X and Y in FIG. 13B, and the band at about 45 KD was observed even at the lowest dosage of retrorsine (35 mg/kg) (See FIG. 13B).

Figure 14:
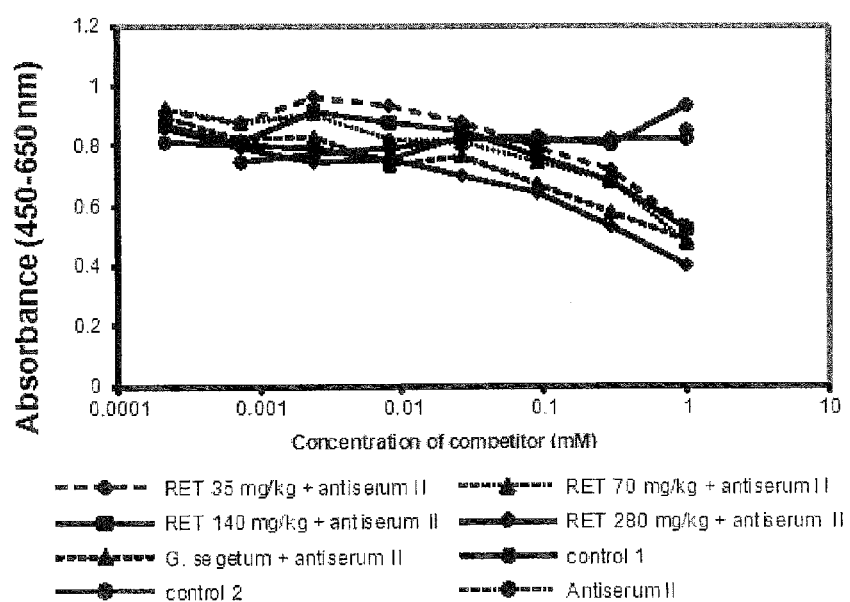
FIG. 14 is a competitive ELISA using rat liver samples as competitors (RET refers to retrorsine).

In competitive ELISA, one hundred microliters of coating antigen, BSA-pyrrole adducts, in PBS buffer was added to wells of a 96-well microtiter plate. The plates were incubated at 4° C. overnight or room temperature for 2 h. Serial dilutions of rat liver samples were prepared in PBST buffer. The resulting solution was mixed (1:1 v/v) with diluted antiserum II in 5% nonfat milk dissolved in PBST buffer. The mixture was incubated at 4° C. overnight. The following day, the same procedure as in the titer analysis was followed. The absorbance at dual wavelength (450-650 nm) was read. The result showed that the liver samples of rats treated with pyrrolizidine alkaloids competitively inhibited the immune response between antiserum II and the coating antigen, while control liver samples had no such inhibitory effect (see FIG. 14).

These results indicated that the raised antibody is capable of detecting the pyrrole-derived protein adduction induced by pyrrolizidine alkaloids in rat model.

Determination of Pyrrole-Protein Adducts in Liver Samples of Mice

Figure 15:
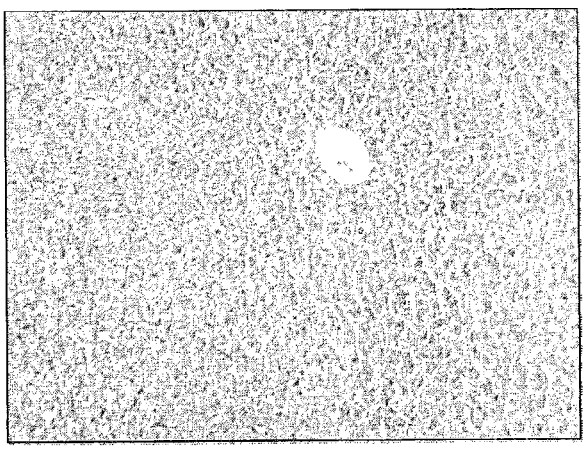
FIG. 15 shows a hematoxylin-eosin (H&E) staining of liver slice of mice. (A) Control; (B) 100 mg/kg retrorsine; (C) 150 mg/kg retrorsine.
Figure 15:
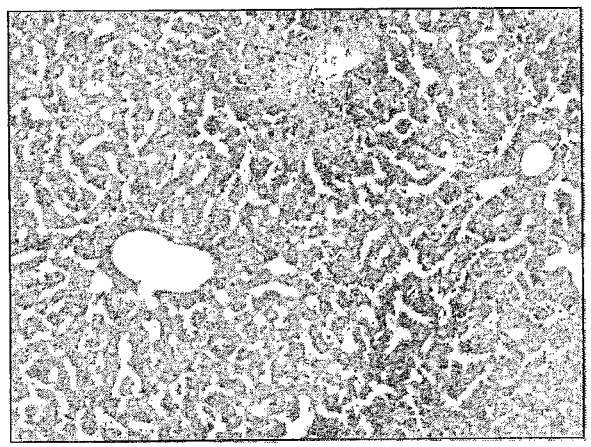
Figure 15:
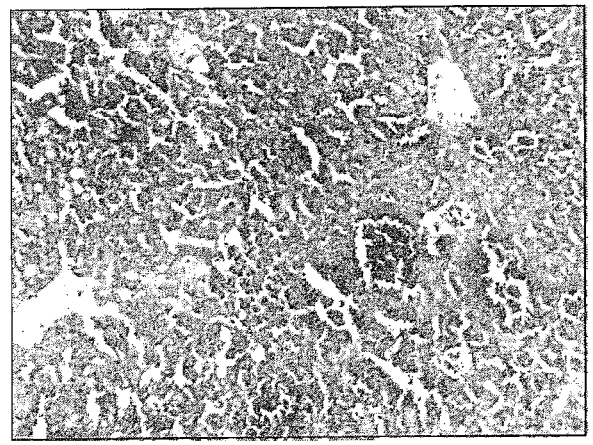

The hepatotoxicity in male CD-1 mice (20-22 g) were also induced in different groups (n=6) via treatment with retrorsine at dosages of 100 and 150 mg/kg, respectively. The pyrrolizidine alkaloid-induced hepatotoxicity in mice was demonstrated by significant serum ALT elevation and also liver injury observed by H&E staining histomorphological assessment (FIG. 15).

Figure 16:
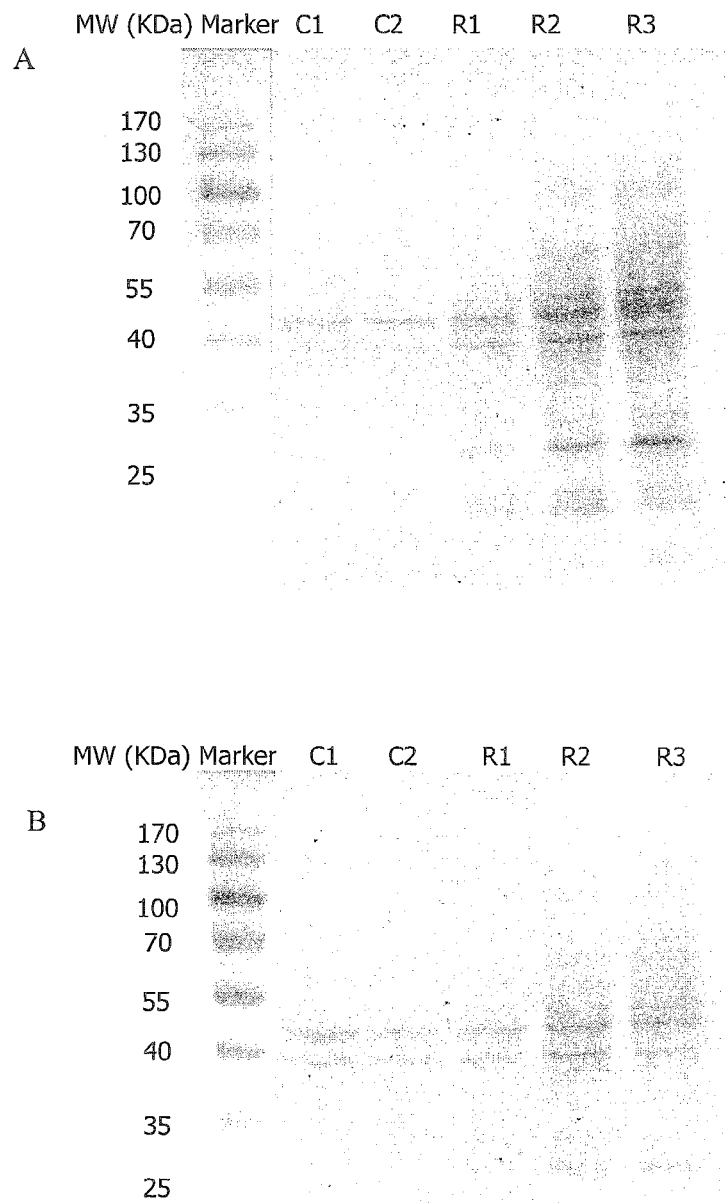
FIG. 16 shows the results of Western blot (A) and competitive Western Blot (B) of mouse liver samples detected by antiserum II using 1 mM lysine-pyrrole as competitor. R1: liver of a mouse treated with retrorsine (100 mg/kg); R2 and R3: liver of 2 mice treated with retrorsine (150 mg/kg); C1 and C2: livers of different control mice.

The hepatotoxicity of pyrrolizidine alkaloids on mice was also assessed by antiserum II, using Western blot and competitive Western blot. The results showed that some protein bands were detected in the liver samples of mice treated with retrorsine but not in those of control mice by antiserum II (FIG. 16A), such as the bands between 20-40 KDa. Furthermore, after pre-incubation of antiserum II with 1 mM lysine-pyrrole adducts, the bands specifically recognized in pyrrolizidine alkaloid-treated mouse liver samples disappeared or their intensity were significantly decreased, while the bands detected in the control samples were not changed (FIG. 16B). The results demonstrated that the antibody specifically recognized the pyrrole moiety in the pyrrole-protein adducts in the mice poisoned by pyrrolizidine alkaloids.

Determination of Pyrrole-Derived Protein Adducts with N-Antibody

The pyrrole-derived protein adduction induced by pyrrolizidine alkaloids on mice was also assessed by purified N-antibody using Western blot, competitive Western blot and immunohistochemical staining.

Figure 17:
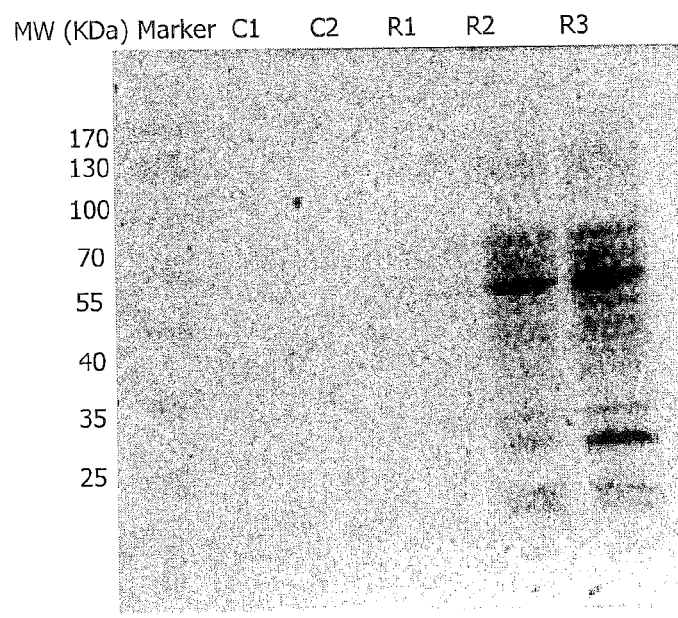
FIG. 17 shows the results of Western blot (A) and competitive Western Blot (B) of mouse liver samples detected by purified N-antibody using 0.5 mM lysine-pyrrole as competitor. R1: liver of a mouse treated with retrorsine (100 mg/kg); R2 and R3: liver of 2 mice treated with retrorsine (150 mg/kg); C1 and C2: livers of different control mice.
Figure 17:
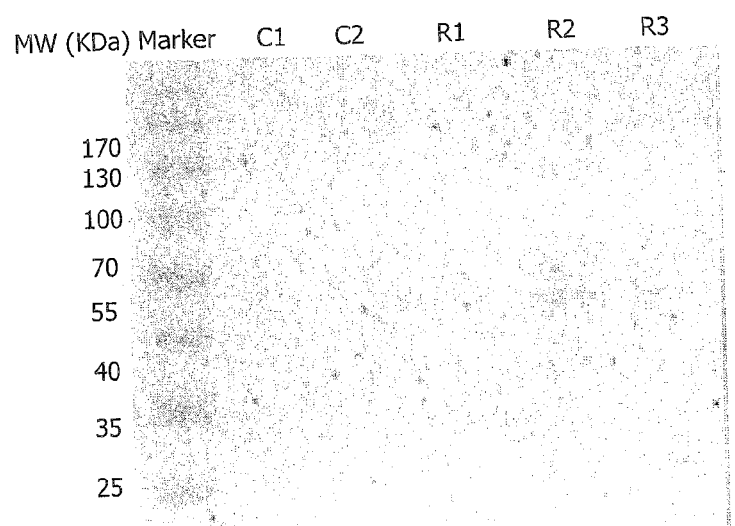

In Western blot assay, the same amount of liver lysates of mice were loaded onto the 7.5% SDS-PAGE. After running and transferring to membrane, the blots were blocked with 5% nonfat milk in PBST buffer for 1 h at room temperature. Blotted membranes were incubated with 1/4500 dilution of purified N-antibody in PBST buffer with 5% nonfat milk at 4° C. overnight. The following day, after washing three times with PBST buffer, membranes were incubated with anti-rabbit IgG-horseradish peroxidase solution (1/5000 in PBST buffer with 5% nonfat milk) for 1 h at room temperature. After washing, protein bands were detected by chemiluminescence with an ECL detection kit. The results are shown in FIG. 17A.

In competitive Western blot assay, the coating antigen was loaded and then transferred to nitrocellulose membranes. After blocked with 5% nonfat milk, the membranes were incubated with 1/4500 dilution of purified N-antibody which was pre-incubated with 0.5 mM lysine-pyrrole at 4° C. overnight. The following day, after washing three times with PBST buffer, membranes were incubated with anti-rabbit IgG-horseradish peroxidase solution (1/5000 in PBST buffer with 5% nonfat milk) for 1 h at room temperature. After washing, protein bands were detected by chemiluminescence with an ECL detection kit. The results are shown in FIG. 17B.

The results showed that when using the purified N-antibody to determine the mouse liver samples, the non-specific protein bands in control samples disappeared, and characteristic protein bands were only detected in the liver samples obtained from pyrrolizidine alkaloid-treated mouse in Western blot assay (FIG. 17A), which were then completely inhibited by pre-incubation of purified antibody with 0.5 mM lysine-pyrrole adduct as competitor (FIG. 17B), demonstrating that the purified N-antibody was specific to recognize the pyrrole moiety in pyrrole-protein adducts.

Figure 18:
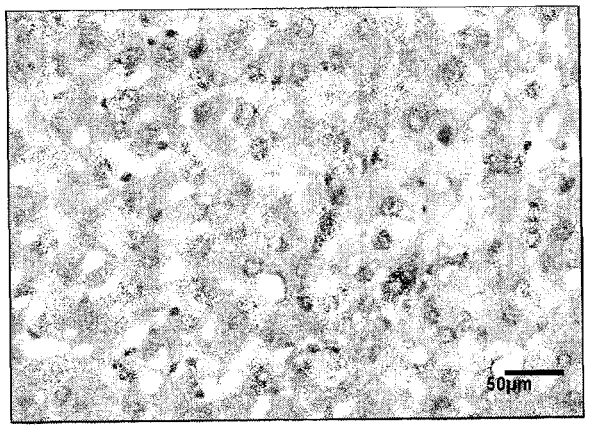
FIG. 18 is an immunochemihistological staining of liver samples obtained from mouse treated with (A) Vehicle; (B) and (C) 100 mg/kg retrorsine; (A) and (B) were detected with purified N-antibody, while (C) was detected with the purified N-antibody pre-incubated with lysine-pyrrole adduct.
Figure 18:
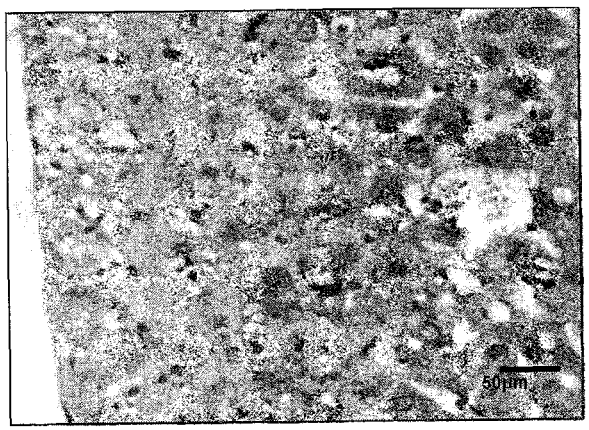
Figure 18:
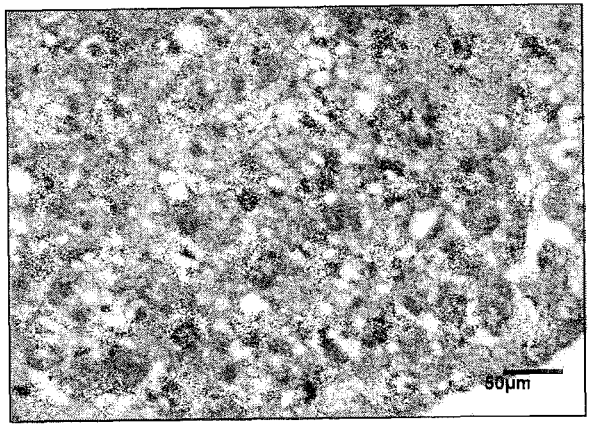

In the immunohistochemical staining, liver injury was observed in the liver slice of mouse treated with 100 mg/kg of retrorsine, and pyrrole-derived protein adduction was observed as the stained spots specifically recognized by the antibody with the intensity significantly higher (FIG. 18B) than that in the control sample (FIG. 18A). Moreover, in the presence of lysine-pyrrole adduct as competitor, the intensity of the stained spots was reduced significantly (FIG. 18C). The immunochemihistological staining results further confirms that the purified N-antibody was specific to recognize the pyrrole moiety, especially the pyrrole-derived protein adducts with N-linkage.

Determination of Pyrrole-Derived Protein Adducts with S-Antibody

The pyrrole-derived protein adduction induced by pyrrolizidine alkaloids on mice was also assessed by purified S-antibody using Western blot assay.

In Western blot assay, the same amount of liver lysates of mice was loaded onto the 7.5% SDS-PAGE. After running and transferring to membrane, the blots were blocked with 5% nonfat milk in PBST buffer for 1 h at room temperature. Blotted membranes were incubated with 1/1500 dilution of purified S-antibody in PBST buffer with 5% nonfat milk at 4° C. overnight. The following day, after washing three times with PBST buffer, membranes were incubated with anti-rabbit IgG-horseradish peroxidase solution (1/5000 in PBST buffer with 5% nonfat milk) for 1 h at room temperature. After washing, protein bands were detected by chemiluminescence with an ECL detection kit.

Figure 19:
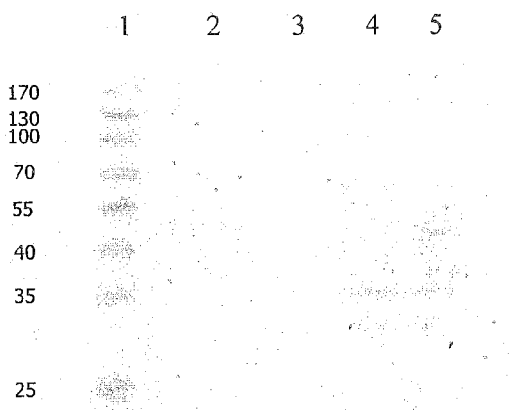
FIG. 19 is the result of Western blot of mouse liver samples detected by S-antibody. Lane 1: Marker; Lane 2 and 3: control; Lane 4 and 5: treated with retrorsine (100 mg/kg).

The results showed that when using the purified S-antibody to determine the mouse liver samples, the non-specific protein bands in control samples disappeared, and characteristic protein bands were only detected in the liver samples obtained from pyrrolizidine alkaloid-treated mouse in Western blot assay (FIG. 19). Moreover, the bands detected by S-antibody were different to that detected by N-antibody (FIG. 17A). These results indicated that the proteins in the pyrrole-derived adducts might be different between the S- and N-linkage, and the purified S-antibody and N-antibody had specificity towards different linkages and were able to selectively detect and distinguish pyrrole-derived protein adducts with S- and N-linkage, respectively.

Determination of Pyrrole-Derived Protein Adducts in Blood Samples of Rats

Figure 20:
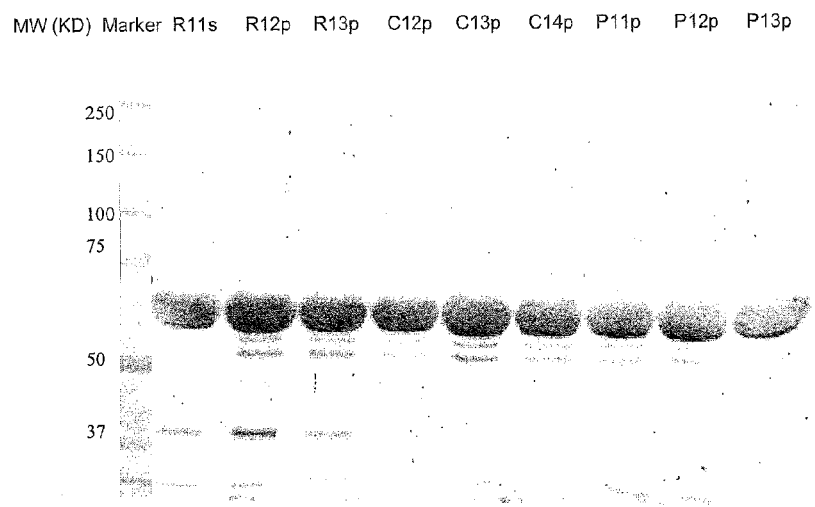
FIG. 20 is the result of Western blot of rat blood samples. R11s, R12p and R13p: serum and plasma of different rats treated with retrorsine (70 mg/kg); C12p, C13p and C14p: plasma of different control rats; P11p, P12p and P13p: plasma of different rats treated with cyclophosphamide (56 mg/kg).

The pyrrole-derived protein adducts in blood samples of rats were also determined with the antibody by Western blot assay. Protein bands were resolved by 7.5% SDS-PAGE and then transferred to nitrocellulose membranes. Before loading, a protein assay was conducted to ensure that an equal amount of protein was loaded. Blots were then blocked with 5% nonfat milk in PBST buffer for 1 h at room temperature. Blotted membranes were incubated with 1/5000 dilution of antiserum II in PBST buffer with 5% nonfat milk at 4° C. overnight. The following day, after washing three times with PBST buffer, membranes were incubated with anti-rabbit IgG-horseradish peroxidase solution (1/3000 in PBST buffer with 5% nonfat milk) for 1 h at room temperature. After washing, protein bands were detected by chemiluminescence with an ECL detection kit. Significant difference was also observed between the blood samples of rats treated with 70 mg/kg of retrorsine and control samples or blood samples of rats treated with cyclophosphamide (56 mg/kg), an anticancer agent can also induce HSOS (hepatic sinusoidal obstruction syndrome) as positive control. The results are shown in FIG. 20. At least one more band at about 40 KD was observed in the retrorsine-treated rat blood samples by comparison with the control and cyclophosphamide-treated samples. However, a non-specific band with strong intensity at about 64 KDa was observed, which might be related to the albumin. Different from liver, the blood exhibit a wide dynamic range of protein abundance, and several proteins, such as albumin, immunoglobulin, fibrinogen and so on, account for approximately 90% of total blood proteins, especially albumin (60%). This might be the reason why the antibody had strong non-specific response with blood samples. Further studies to solve this problem by removing non-specific albumin in the blood sample or developing monoclonal antibody are warranted. While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

REFERENCES

Fu, P. P.; Xia, Q.; Lin, G.; Chou, M. W. Pyrrolizidine alkaloids: genotoxicity, metabolism enzymes, metabolic activation, and mechanisms. Drug Metab. Rev. 2004, 36, 1-55.

Lin, G.; Wang, J. Y.; Li, N.; Li, M.; Gao, H.; Ji, Y.; Zhang, F.; Wang, H. L.; Zhou, Y.; Ye, Y.; Xu, H. X.; Zheng, J. Hepatic sinusoidal obstruction syndrome associated with consumption of *Gynura segetum*. J. Hepatol. 2011, 54, 666-673.

Lin G, Cui Y Y, Hawes E M. Characterization of rat liver microsomal metabolites of clivorine, a hepatotoxic otonecine-type pyrrolizidine alkaloid. Drug Metab. Disp. 2000, 28, 1475-1483.

What is claimed is:

1. An antibody, comprising a binding site which specifically recognizes a pyrrole moiety conjugated to a cellular macromolecule, and being raised in a mammal administered with a synthetic immunogen comprising the pyrrole moiety as hapten conjugated to a carrier protein, wherein the pyrrole moiety has the structure

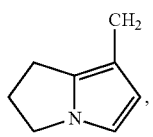

and the antibody has no cross-reactivity with monocrotaline and retrorsine.

2. The antibody of claim 1, wherein said cellular macromolecule is a protein.

3. The antibody of claim 1, wherein said carrier protein is keyhole limpet hemocyanin (KLH).

4. The antibody of claim 1, wherein said mammal is a rabbit.

5. An assay kit for detecting or diagnosing pyrrolizidine alkaloid poisoning, comprising an antibody having an antigen binding site specifically recognizing a pyrrole moiety conjugated to a cellular macromolecule, wherein said pyrrole moiety has the structure

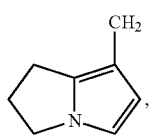

and the antibody has no cross-reactivity with monocrotaline and retrorsine.

6. The assay kit of claim 5, wherein said macromolecule is a protein.

7. The antibody of claim 1, which is a monoclonal antibody or a polyclonal antibody.

8. The antibody of claim 1, wherein said synthetic immunogen is selected from the group consisting of:

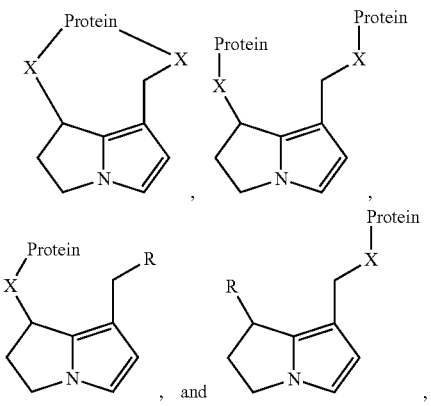

and combinations thereof,
wherein X comprises N or S; and R is selected from a group consisting of —OH and an alkyl group.

9. The antibody of claim 1, wherein the pyrrole moiety is conjugated to a protein via a nitrogen-containing linkage (N-linkage), and the antibody specifically recognizes the pyrrole moiety conjugated to a protein via an N-linkage.

10. The antibody of claim 1, wherein the pyrrole moiety is conjugated to a protein via a sulfur-containing linkage (S-linkage), and the antibody specifically recognizes the pyrrole moiety conjugated to a protein via an S-linkage.

11. The assay kit of claim 5, wherein the pyrrole moiety conjugated to a cellular macromolecule is selected from the group consisting of:

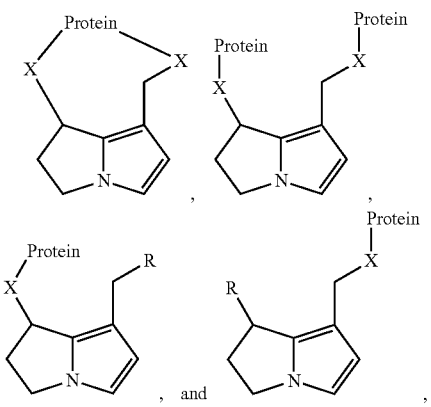

and combinations thereof,
wherein
X comprises N or S; and
R is selected from a group consisting of —OH and an alkyl group.

12. The assay kit of claim 5, wherein the pyrrole moiety is conjugated to a protein via a nitrogen-containing linkage (N-linkage), and the antibody specifically recognizes the pyrrole moiety conjugated to a protein via an N-linkage.

13. The assay kit of claim 5, wherein the pyrrole moiety is conjugated to a protein via a sulfur-containing linkage (S-linkage), and the antibody specifically recognizes the pyrrole moiety conjugated to a protein via an S-linkage.

* * * * *

UNITED STATES PATENT AND TRADEMARK OFFICE
CERTIFICATE OF CORRECTION

PATENT NO. : 9,056,916 B2
APPLICATION NO. : 13/354341
DATED : June 16, 2015
INVENTOR(S) : Ge Lin It is certified that error appears in the above-identified patent and that said Letters Patent is hereby corrected as shown below:

In the Claims:

Claim 6, Column 13, Line 63 – insert --cellular-- after "said" and before "macromolecule".

Signed and Sealed this
Twelfth Day of April, 2016

Michelle K. Lee
*Director of the United States Patent and Trademark Office*